United States Patent
O'Lenick, Jr.

(10) Patent No.: US 6,800,741 B1
(45) Date of Patent: Oct. 5, 2004

(54) ALKOXYLATED SURFACTANTS BASED UPON ALKYL POLYGLYCOSIDE

(75) Inventor: Anthony J. O'Lenick, Jr., Dacula, GA (US)

(73) Assignee: Colonial Chemical Inc., South Pittsburg, TN (US)

( * ) Notice: Subject to any disclaimer, the term of this patent is extended or adjusted under 35 U.S.C. 154(b) by 0 days.

(21) Appl. No.: 10/616,678

(22) Filed: Jul. 11, 2003

Related U.S. Application Data

(63) Continuation-in-part of application No. 10/261,117, filed on Oct. 1, 2002, now Pat. No. 6,627,612.

(51) Int. Cl.$^7$ .......................... C07H 15/04; C07H 15/08
(52) U.S. Cl. ...................... 536/4.1; 536/120; 536/123.1
(58) Field of Search ...................... 536/4.1, 120, 123.1; 514/25

(56) References Cited

U.S. PATENT DOCUMENTS

| 5,003,057 A | | 3/1991 | McCurry | |
| 5,428,142 A | * | 6/1995 | O'Lenick, Jr. | 536/1.11 |
| 5,498,703 A | * | 3/1996 | O'Lenick, Jr. | 536/4.1 |

* cited by examiner

Primary Examiner—James O. Wilson
Assistant Examiner—Michael C. Henry

(57) ABSTRACT

The invention relates to a series of polyglycoside derivatives that have improved water-solubility by introducing into the molecule polyoxyalkylene groups like polyoxyethylene and polyoxypropylene. The compounds are very mild detergents and emulsifiers.

1 Claim, No Drawings

ALKOXYLATED SURFACTANTS BASED UPON ALKYL POLYGLYCOSIDE

RELATED APPLICATION

This application is a continuation in part of application of Ser. No. 10/261,117 filed Oct. 1, 2002 now U.S. Pat. No. 6,627,612.

FIELD OF THE INVENTION

The present invention relates to a series of polyglycoside derivatives that contain water-soluble groups introduced into the molecule by reaction with the hydroxyl groups present in the molecule. The preferred products have more than one water-soluble group per molecule and are made with mild reagents to avoid discoloration and mal odor.

Commercial alkyl polyglycosides generally have a low degree of polymerization of polysaccharide, in the molecule. This results in a molecule that is of limited water solubility. The present invention is aimed at functionalizing the hydrophobic alkyl polyglycoside, by including in the molecule polyoxyalkylene groups selected from polyoxyethylene, and polyoxypropylene both of which provide improved water solubility and improved surfactant properties.

BACKGROUND

Alkyl polyglycosides have been known for many years, having been first synthesized in the early 1900 by Emile Fischer. Despite this, the products were of little commercial interest until much later.

U.S. Pat. No. 4,393,203 issued Jul. 12, 1983 to Mao et al, incorporated herein by reference, disclose that long chain fatty alcohols can be removed from alkyl polysaccharide products in thin film evaporators to achieve fatty alcohol levels of less than about 2% without excessive discoloration of the alkyl polysaccharide. This allowed for a more cosmetically acceptable product to be developed that is more surface active. The presence of the free fatty alcohol in the mixture, allows for a more water-soluble product, by removing the water insoluble alcohol.

One of the most significant patents is U.S. Pat. No. 5,003,057 issued Mar. 26, 1991 to McCurry et al incorporated herein by reference, provides for a process for preparing glycosides from a source of saccharide moiety and an alcohol in the presence of a hydrophobic acid catalyst is provided. An example of such a catalyst is dinonylnaphthalenemonosulfonic acid. The use of such catalysts provides a number of process advantages, which includes the reduced production of polar by-products. Preferred glycosides produced by the process are higher alkyl glycosides useful as surfactants.

U.S. Pat. No. 3,598,865 (Lew) discloses the production of higher alkyl ($C_{-8}$–$C_{25}$) glycosides from a monosaccharide or source thereof and a higher monohydric alcohol in the presence of a latent solvent (lower alcohols) and an acid catalyst selected from the group consisting of sulfuric acid, hydrochloric acid, phosphoric acid, phosphorous acid, toluenesulfonic acid, and boron trifluoride.

U.S. Pat. No. 3,219,656 (Boettner) discloses a process for producing a higher alkyl glycoside by reacting glucose with methanol in the presence of a macroreticular-structured sulfonic acid resin, anhydrous and in the acid form, to produce methyl glycoside which is reacted without isolation with butanol to form butyl glycoside and which in turn is reacted with a higher alcohol to form a surface active higher alkyl glycoside.

U.S. Pat. No. 3,839,319 (Mansfield) discloses a process for producing alkyl glycosides by direct, acid catalyzed reaction of a higher alcohol and a saccharide. The acid catalysts are mineral acids such as hydrochloric and sulfuric, and sulfonic acid exchange resins An excellent review article was written by Barry Salka of Henkel Corporation in Vol. 108 p89–93 covering the chemistry and applications of alkyl glycosides in a variety of formulations. Salka points out that the degree of polymerization of glycoside is 1.4 on commercial products. This means that there are on average only 1.4 glucose units per alkyl group, resulting in a hydrophobic material. This significantly limits the suitability of this type of molecule in many applications, particularly in personal care and cosmetic applications. In fact commercial the predominant species in the commercial mixture (about 70% by weight) is the water insoluble mono product.

None of the patents referenced above provide for a molecule that has the necessary water soluble group incorporated to overcome the lack of water solubility, greasy drying feel that alkyl glycosides have on the skin.

The Invention

The present invention relates to the finding that the reaction of the rather hydrophobic alkyl polyglycosides with the proper reagent results in molecules that have improved water-solubility and consequently overcome many of the shortcomings of the alkyl polyglycosides itself. It is most interesting that the maximum amount of glycoside units per alkyl group that can be added using known technology is 1.5. This means that the product is a mixture of mono and di functional product. This product has the remaining fatty alcohol stripped off in an evaporative process. The resulting product is about 70% by weight of a product of a d.p. of 1, about 21% by weight of a product of a d.p. of 2, about 7% by weight of a product having a d.p. of 3, and about 2% by weight of a product that has a d.p. of 4.

We have surprisingly learned that taking the alkyl polyglycosides produced in the commercial process, with it's inherent lack of water solubility and reacting it to make non-ionic surface-active agents, results in a series of products that are much more usable in many applications. Simply put, alkyl polyglycosides make much better hydrophobic raw materials than finished surface-active agents. When some or all of the many hydroxyl groups are converted into cationic groups outstanding conditioning and water solubility results.

SUMMARY OF THE INVENTION

Alkyl polyglycosides are complex products made by the reaction of glucose and fatty alcohol. In dealing with the chemistry one talks about degree of polymerization (the so called "d.p."). In the case of traditional alkyl polyglycosides the d.p. is around 1.4. This means that on average thee is 1.4 units of glucose for each alkyl group. The fact of the matter is that the resulting material is a mixture having an average of 1.4.

The specific structure of the product is hard to ascertain completely since many positional isomers are possible, but two examples of structures are as follows;

$$RO-(H)C\overset{O}{\underset{|}{\diagdown}}C(H)-CH_2-OH$$
$$HO-(H)C\underset{|}{\diagup}C(H)-OH$$
$$\overset{|}{OH}\overset{|}{H}$$

Alkyl polyglycosides (d.p. 1)

$$RO-(H)C\overset{O}{\diagdown}C(H)-CH_2-OH$$
$$HO-(H)C\diagup C(H)-OH$$
$$H\quad O$$
$$\quad\quad |$$
$$\quad\quad CH_2$$
$$HO-(H)C\overset{O}{\diagdown}C-H$$
$$HO-(H)C\diagup C(H)-OH$$
$$OH\quad H$$

Alkyl polyglycosides (d.p. 2)

It should be clear that if there is a 50/50 mixture of the d.p. 1 and d.p. 2 product, the resulting analytical data will show that on average there is a d.p. of 1.5. Saying that a molecule has a d.p. of 1.5 does not mean that each molecule has 1.5 glucose units on it.

One key aspects of the present invention relates to the heretofore unappreciated fact that the rather hydrophobic alkyl polyglycosides contain on average five hydroxyl groups, one primary and the other four secondary. The assumption that there is a large degree of group specificity for the primary to react exclusively rather than the four additional hydroxyl groups is simply not true. This means that if on average only one of the five groups is reacted, there remains a very large concentration of reacting alkyl polyglycoside that has no functionality on it. Since the reactant with no functionalization remain water insoluble, there needs to be at lease 2 and as many as 4 hydroxyl groups functionalized to get to the desired water-soluble product. We have observed that when between 2 and 5 groups are reacted, a water-soluble very useful product results. Therefore it is a preferred embodiment having between 2 and 5 of the hydroxyl groups functionalized.

Another key unappreciated fact in making the compounds of the present invention is the fact that the alkoxylation reaction can if carried out in water using base catalyst results in a composition that contains (a) mono-glycoside alkoxylates, di-glycoside, (c) polyoxyalkylene glycol and the exact mixture of these compositions are key to the functionality of the products of the current invention.

DETAILED DESCRIPTION OF THE INVENTION

The compositions of the present invention are mixtures conform to the following structures:

(a)
$$RO-(H)C\overset{O}{\diagdown}C(H)-CH_2-OR^4$$
$$R^3O-(H)C\diagup C(H)-OR^1$$
$$\overset{|}{OR^2}\overset{|}{H}$$

wherein;

R is alkyl having 8 to 22 carbon atoms;

$R^1$, $R^2$, $R^3$ and $R^4$ are independently selected from the group consisting of $$-(CH_2CH_2O)_x-(CH_2CH(CH_3)-O)_y-(CH_2CH_2O)_z-H$$

and H, with the proviso that $R^1$, $R^2$, $R^3$, and $R^4$ are not all H;

x, y and z are independently integers ranging from 0 to 20, with the proviso that x+y+z be at least 1;

and (b)
$$RO-(H)C\overset{O}{\diagdown}C(H)-CH_2-OR^6$$
$$R^7O-(H)C\diagup C(H)-OR^5$$
$$H\quad O$$
$$\quad\quad |$$
$$\quad\quad CH_2$$
$$R^8O-(H)C\overset{O}{\diagdown}C-H$$
$$R^9O-(H)C\diagup C(H)-OR^{11}$$
$$\overset{|}{OR^{10}}\overset{|}{H}$$

wherein;

R is alkyl having 8 to 22 carbon atoms;

$R^1$, $R^2$, $R^3$ and $R^4$, $R^5$, $R^6$, $R^7$ $R^8$, $R^9$, $R^{10}$, and $R^{11}$ are independently selected from the group consisting of $$-(CH_2CH_2O)_x-(CH_2CH(CH_3)-O)_y-(CH_2CH_2O)_z-H$$

$$-(CH_2CH_2O)_x-(CH_2CH(CH_3)-O)_y-(CH_2CH_2O)_z-H$$

and H, with the proviso that $R^1$, $R^2$, $R^3$, and $R^4$ are not all H;

x, y and z are independently integers ranging from 0 to 20, with the proviso that x+y+z be at least 1;

and $$H-(CH_2CH_2O)_x-(CH_2CH(CH_3)-O)_y-(CH_2CH_2O)_z-H$$

x, y and z are independently integers ranging from 0 to 20, with the proviso that x+y+z be at least 1.

Another aspect of the present invention is a process for cleansing hair and skin which comprises contacting the hair and skin with an effective detersive concentration of a composition conforming to the following:

(a)

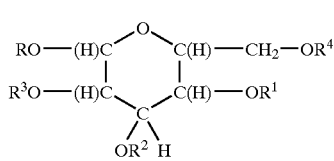

wherein;
R is alkyl having 8 to 22 carbon atoms;
$R^1, R^2, R^3$ and $R^4$ are independently selected from the group consisting of

and H, with the proviso that $R^1, R^2, R^3$, and $R^4$ are not all H;
x, y and z are independently integers ranging from 0 to 20, with the proviso that
x+y+z be at least 1;
and (b)

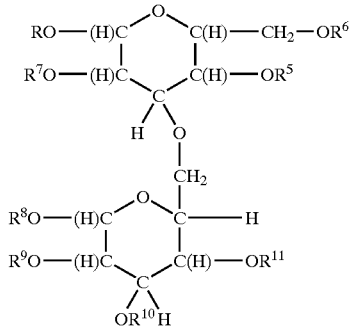

wherein;
R is alkyl having 8 to 22 carbon atoms;
$R^1, R^2, R^3$ and $R^4, R^5, R^6, R^7$ $R^8, R^9, R^{10}$, and $R^{11}$ are independently selected from the group consisting of

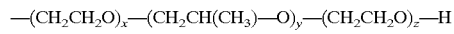

and H, with the proviso that $R^1, R^2, R^3$, and $R^4$ are not all H;
x, y and z are independently integers ranging from 0 to 20, with the proviso that
x+y+z be at least 1;
and

x, y and z are independently integers ranging from 0 to 20, with the proviso that
x+y+z be at least 1
said detersive concentration ranges from 0.1 to 50% by weight.

Since the composition of the present invention is a complex mixture, another aspect of the present invention is a product by process. An alkoxylated polyglucoside which is prepared by the reaction of:

(a)

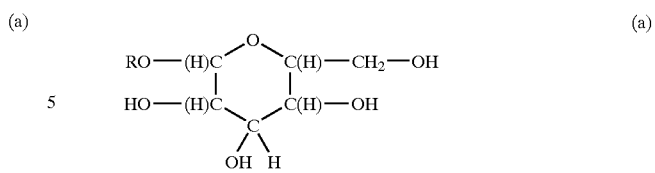

wherein;
R is alkyl having 8 to 22 carbon atoms;
and (b)

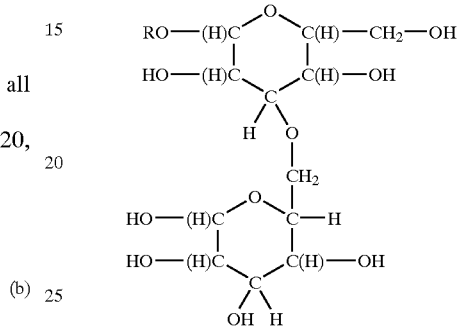

wherein;
R is alkyl having 8 to 22 carbon atoms;
and
(c) $H_2O$
with
ethylene oxide, propylene oxide or mixtures thereof in the presence of an alkaline catalyst selected from the group consisting of KOH, NaOH or $CH_3ONa$ Preferred Embodiments In a preferred embodiment n is 0.
In a preferred embodiment n is 11.
In a preferred embodiment n is 13.
In a preferred embodiment n is 17.
In a preferred embodiment n is 19.
In a preferred embodiment n is 21.
In a preferred embodiment the % by weight of water ranges from 10–50%.
In another preferred embodiment the % by weight of water ranges from 20–30%.
In another preferred embodiment the % by weight of water is 25%.
In a preferred embodiment the % by weight of polyglycoside ranges from 90–50%.
In another preferred embodiment the % by weight of polyglycoside ranges from 80–70%.
In another preferred embodiment the % by weight of polyglycoside is 75%.

EXAMPLES

Preparation of Alkyl Glycosides

Alkyl Glycosides are raw materials used to make the surface-active polyglycoside derivatives of the present invention.

Saccharides useful in the process of making alkyl glycosides are saccharides that can be alkylated in the "1" position, commonly referred to as "reducing saccharides", or higher saccharides that can be hydrolyzed to provide such a saccharide. These saccharides are typically comprised of aldo- or keto-hexoses or pentoses.

Examples of saccharides include glucose (dextrose), fructose, mannose, galactose, talose, allose, altrose, idose, arabinose, xylose, lyxose, and ribose. Examples of hydrolyzable saccharides that are a source of reducing saccharides include starch, maltose, sucrose, lactose, maltotriose, xylobiose, mellibiose, cellobiose, raffinose, stachiose, methyl glycosides, butyl glycosides, levoglucosan, and 1,6-anhydroglucofuranose.

The physical form of the saccharide may vary. The saccharide will typically be in a fluid (as opposed to a solid) state, e.g. as a melt or an aqueous syrup, during at least a portion of the period of reaction, if not for a predominant portion of the period of the reaction. Crystalline (e.g. anhydrous or hydrates) or amorphous saccharide solids in various particle sizes, e.g. granules, powders, etc., can be used, but the heating of the reaction medium may well fluidize at least a portion of a solid reactant, if not a predominant portion of the saccharide reactant. Aqueous syrups of saccharides, typically at saccharide solids of between about 10% and 90% dry solids by weight can also be used. Indeed, the use of the hydrophobic catalysts of this invention should show the most improved results over conventional catalysts in the context of the use of aqueous syrup reactants as compared with processes which employ solid saccharide reactants, particularly with respect to avoiding the formation of deleterious amounts of polysaccharides and very high DP alkyl glycosides during the glycoside formation reaction.

The preferred saccharides are glucose, galactose, xylose and arabinose, or mixtures thereof, for reasons of availability, low cost, and convenience. Glucose in the anhydrous crystalline form is preferred, although dextrose monohydrate, corn syrups of high dry solids (typically 50% to 80% dry solids) and a high dextrose equivalence (D.E.) (typically greater than 90 D.E and most commonly 95 D.E.) can be commonly employed. Indeed, while the higher the purity of the dextrose source, the better the quality of the product (other things being equal), the catalysts of this invention allow the use of a lower purity dextrose source and yet yield a product of substantially equivalent quality as compared with prior catalysts. Because of the ready availability of glucose and its oligomers, much of the remaining description is particularly suited to the use of glucose in its various forms.

Alcohols useful in the process of this invention are hydroxyl-functional organic compounds capable of alkylating a saccharide in the "1" position. The alcohol can be naturally occurring, synthetic, or derived from natural sources and/or derivatized. Examples include monohydric alcohols (more fully discussed below) and polyhydric alcohols (e.g. ethylene glycol, propylene glycol, polyethylene glycols, polypropylene glycols, butylene glycol, glycerol, trimethylolpropane, pentaerythritol, polyester polyols, polyisocyanate polyols, and so on). Other examples include aromatic alcohols such as benzyl alcohol, phenol, substituted phenols (e.g. alkylphenols) and alkoxylates of each.

Preferred alcohols are monohydric alcohols containing from about 1 to about 30 carbon atoms. They may be primary or secondary alcohols, straight or branched chain, saturated or unsaturated (e.g. allyl alcohol, 2-ethylhexenyl alcohol and oleyl alcohol) alkyl or aralkyl alcohols, ether alcohols, cyclic alcohols, or heterocyclic alcohols. In general, these alcohols have minimal solvent power for the saccharide molecule. Examples of the monohydric alcohols which may be employed in the present invention include methyl alcohol, isopropyl alcohol, butyl alcohol, octyl alcohol, nonyl alcohol, decyl alcohol, dodecyl alcohol, tridecyl alcohol, tetradecyl alcohol, pentadecyl alcohol, hexadecyl alcohol, pentacosyl alcohol, oleyl alcohol, linoleyl alcohol, isoborneol alcohol, hydroabietyl alcohol, phenoxyethanol, phenoxypolyethoxyethanol containing five ethoxy groups, 2-methyl-7-ethyl-4-undecanol, and mixtures of one or more of the above.

A preferred group of alcohols are alkanols having the formula ROH wherein R represents an alkyl group having from 8 to 30 carbon atoms. A particularly preferred group of alcohols are those wherein R represents an alkyl radical having from 8 to 20, preferably 11 to 18, carbon atoms. The alkyls can be straight or branched chain.

ALKYL GLYCOSIDE EXAMPLES

Example 1

A one-liter, four-necked, round-bottomed flask was equipped through its center neck with an overhead mechanical stirrer, through a second neck with a distillation head fitted with an addition funnel and a condenser/receiver/vacuum take-off assembly, through a third neck fitted with a three hole rubber stopper with a capillary nitrogen bleed, a calibrated mercury thermometer and a vacuum tight temperature controller probe, and on the fourth neck with a septum for sampling.

The flask was charged with 602.4 g (3.105 moles) of a commercial mixture of $C_{11}$ to $C_{15}$ (98% $C_{12}$ and $C_{13}$) straight and branched alkanols (Neodol 23 available form Shell Chemical Co.) and 136.6 g (0.69 moles) of a commercially available dextrose monohydrate (Staleydex 333, available from A. E. Staley Mfg. Co. at 9.0% moisture). The slurry was heated at a vacuum of 30 mm Hg (absolute). Water was released starting at about 57.degree. C. and heating was continued until the slurry had reached 110.degree. C. At this time 3.2 g (0.00345 mole of a commercially available mixture of 50% dinonylnaphthalenesulfonic acid in heptane (available from King Industries) was added as a catalyst and the theoretical volume of water distilled at about a linear rate over 8 hours. After stirring an additional hour, a stoichiometric amount of aqueous NaOH (33% in $H_2O$) was added. An aliquot of the neutralized reaction mixture (3.39 g, 1 g dissolved substance) was dissolved in a total volume of 10 ml with 1:1 isopropanol:water. The pH of this solution was 7.8.

The remainder of the reaction mixture was evaporated to a clear melt at 200.degree. C. and 1 mm pressure using a Leybold-Heraeus Distact.TM. wiped film evaporator operating at a feed rate of 700 ml/hr.

The residue was analyzed using a combination of gas and liquid chromatographic techniques as well as NMR spectroscopy and was shown to contain less than 0.2% free alcohol and less than 2% polar species (HPLC) and an NMR mole ratio of glucose rings to fatty chains of about 1.4.

Examples 2–9

The same one-liter, four-necked, round-bottomed flask was equipped through its center neck with an overhead mechanical stirrer, through a second neck with a distillation head fitted with an addition funnel and a condenser/receiver/vacuum take-off assembly, through a third neck fitted with a three hole rubber stopper with a capillary nitrogen bleed, a calibrated mercury thermometer and a vacuum tight temperature controller probe, and on the fourth neck with a septum for sampling.

The flask was charged with 3.105 moles of the specified alcohol and 136.6 g (0.69 moles) of a commercially available dextrose monohydrate (Staleydex 333, available from A. E. Staley Mfg. Co. at 9.0% moisture). The slurry was heated at a vacuum of 30 mm Hg (absolute). Water was released starting at about 57.degree. C. and heating was continued until the slurry had reached 110.degree. C. At this time 3.2 g (0.00345 mole of a commercially available mixture of 50% dinonylnaphthalenesulfonic acid in heptane (available from King Industries) was added as a catalyst and the theoretical volume of water distilled at about a linear rate over 8 hours. After stirring an additional hour, a stoichiometric amount of aqueous NaOH (33% in $H_2O$) was added. An aliquot of the neutralized reaction mixture (3.39 g, 1 g dissolved substance) was dissolved in a total volume of 10 ml with 1:1 isopropanol:water. The pH of this solution was 7.8.

The remainder of the reaction mixture was evaporated to a clear melt at 200.degree. C. and 1 mm pressure using a Leybold-Heraeus Distact.TM. wiped film evaporator operating at a feed rate of 700 ml/hr. The residue was analyzed using a combination of gas and liquid chromatographic technique as well as NMR spectroscopy and was shown to contain less than 0.2% free alcohol and less than 2% polar species (HPLC) and an NMR mole ratio of glucose rings to fatty chains of about 1.4. The hydroxyl value was run on the resultant product and is indicated below.

| Example | Alkyl  | OH Value |
|---------|--------|----------|
| 2       | C12H25 | 691.9    |
| 3       | C10H21 | 741.8    |
| 4       | C8H17  | 795.4    |
| 5       | C14H27 | 653.8    |
| 6       | C18H37 | 584.4    |
| 7       | C18H35 | 586.7    |
| 8       | C20H42 | 555.1    |
| 9       | C22H42 | 531.2    |

Alkyl Polyglycoside Alkoxylates Compounds

There are a member of water-soluble groups that can be introduced into the finished alkyl polyglycoside, these include polyoxyethylene and polyoxypropylene, The reaction of a the polyglycoside is conducted with 25% water present. This results in a composition as specified, containing mono-glycoside alkoxylate, di-glycoside alkoxylate, since the product subjected to alkoxylation is in fact a mixture of the two, and an poly-oxyalkylene polymer of the EO/PO block type that results from alkoxylation of the water present. This component of the composition is critically important to the solubility of the composition, resulting in products that are more soluble per added increment of EO or PO group. EO is ethylene oxide, which results in a —$CH_2CH_2O$— linkage, PO is propylene oxide, which results in a —$CH_2$—$CH(CH_3)$—O— linkage.

The water is consumed under base catalysis to give an alkoxylate:

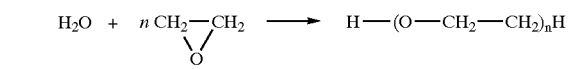

Since the water and the hydroxyl groups of the polyglycoside all react, a mixture is achieved. This composition has very desirable properties.

It will be clearly understood that the alkyl polyglycoside alkoxylates of the present invention have a number of hydroxyl groups present in the molecule. The number of hydroxyl groups functionalized will have a profound effect upon the degree of increased water solubility of the molecule.

The present invention includes a functionalization of a low number of hydroxyl groups (one per molecule) to a high number (all groups on the molecule). The preferred number to functionalize is an intermediate number of groups (approximately half of the number present).

Reaction

The reactants useful in the synthesis of the products of the current invention are commercially available from a variety of sources. They are ethylene oxide and propylene oxide. The reaction is run under base catalysis with NaOH, KOH or $NaOCH_3$.

General Alkoxylation Procedure

To a clean, dry reaction flask, capable or containing a pressure of 100 psig, equipped with agitation, thermometer and an ability to inject a pre-weighed amount of propylene oxide, ethylene oxide or combinations thereof, is added the specified amount of the specified polyglycoside (example 1–9). Adjust the amount if water present to 25% by weight, either by addition of water or distillation of water from the product. Next add 0.1% by weight KOH flake to the reactor, with the agitation. The 0.1% by weight is based upon the weight of the final product including the EO and PO to be added. Add ethylene oxide or propylene oxide at 300–310° F. and 45 psig.

It will be clearly understood that the alkyl polyglycoside has on average five hydroxyl groups when the d.p. is 1.4. There is also water present. The reaction can occur on several of the groups resulting in a composition

Examples 10–26

|         | Alkyl polyglycoside |        | Ethylene Oxide | Propylene Oxide | Ethylene Oxide |
|---------|---------|--------|----------|----------|----------|
| Example | Example | Grams  | Grams    | Grams    | Grams    |
| 10      | 1       | 446.0  | 44.0     | 59.0     | 44.0     |
| 11      | 2       | 416.0  | 88.0     | 590.0    | 0.0      |
| 17      | 3       | 388.0  | 440.0    | 120.0    | 880.0    |

-continued

| | Alkyl polyglycoside | | Ethylene Oxide | Propylene Oxide | Ethylene Oxide |
|---|---|---|---|---|---|
| Example | Example | Grams | Grams | Grams | Grams |
| 12 | 4 | 472.0 | 880.0 | 1180.0 | 880.0 |
| 13 | 5 | 528.0 | 44.0 | 0.0 | 0.0 |
| 14 | 6 | 526.0 | 500.0 | 0.0 | 440.0 |
| 15 | 7 | 446.0 | 200.0 | 590.0 | 88.0 |
| 16 | 8 | 416.0 | 350.0 | 0.0 | 0.0 |
| 17 | 9 | 388.0 | 35.0 | 59.0 | 44.0 |
| 18 | 1 | 472.0 | 0.0 | 590.0 | 0.0 |
| 19 | 2 | 528.0 | 0.0 | 59.0 | 0.0 |
| 20 | 3 | 526.0 | 0.0 | 1180.0 | 880.0 |
| 21 | 4 | 472.0 | 0.0 | 592.0 | 880.0 |
| 22 | 5 | 528.0 | 880.0 | 1180.0 | 880.0 |
| 23 | 6 | 526.0 | 88.0 | 59.0 | 88.0 |
| 24 | 7 | 446.0 | 880.0 | 1180.0 | 0.0 |
| 25 | 8 | 416.0 | 440.0 | 59.0 | 440.0 |
| 26 | 9 | 388.0 | 0.0 | 0.0 | 44.0 |

The compounds are typically clear yellow liquids to pastes. The compositions are good detergents emulsifiers. They are well suited to the personal care market.

These compositions are of particular importance for use in personal care application like bubble bath, shampoos and body wash. They are also very good additives for hard surface cleaners and detergent systems.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. An alkoxylated polyglycoside which comprises a mixture conform to the following structures:

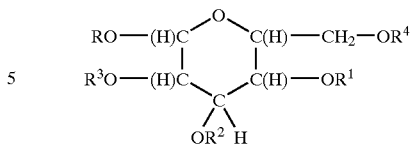

(a)

wherein;
R is alkyl having 8 to 22 carbon atoms;
are independently selected from the group consisting of $$-(CH_2CH_2O)_x-(CH_2CH(CH_3)-O)_y-(CH_2CH_2O)_z-H$$

and H, with the proviso that $R^5, R^6, R^7, R^8, R^9, R^{10}$ and $R^{11}$ are not all H;
x, y and z are independently integers ranging from 0 to 20, with the proviso that
x+y+z be at least 1 and

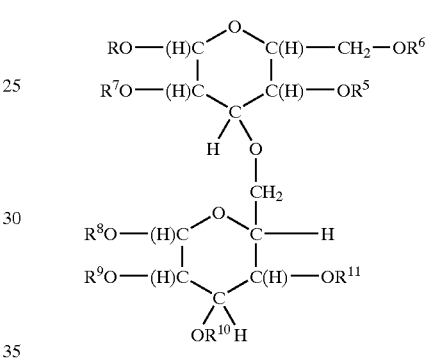

(b)

wherein;
R is alkyl having 8 to 22 carbon atoms;
$R^1, R^2, R^3$ and $R^4, R^5, R^6, R^7$ $R^8, R^9, R^{10}$, and $R^{11}$ are independently selected from the group consisting of $$-(CH_2CH_2O)_x-(CH_2CH(CH_3)-O)_y-(CH_2CH_2O)_z-H$$

and H, with the proviso that $R^1, R^2, R^3$, and $R^4$ are not all H;
x, y and z are independently integers ranging from 0 to 20, with the proviso that
x+y+z be at least 1.

* * * * *